United States Patent [19]
Lee

[11] Patent Number: 5,788,569
[45] Date of Patent: Aug. 4, 1998

[54] METHOD AND APPARATUS FOR DEODORIZING THE INTERIOR OF A ROOM AIR CONDITIONER

[75] Inventor: Gab-Youl Lee, Suwon, Rep. of Korea

[73] Assignee: Samsung Electronics Co., Ltd., Suwon, Rep. of Korea

[21] Appl. No.: 647,748

[22] Filed: May 15, 1996

[30] Foreign Application Priority Data

May 18, 1995 [KR] Rep. of Korea ............. 1995-12426

[51] Int. Cl.⁶ ............................................. F24F 6/00
[52] U.S. Cl. ..................... 454/233; 62/78; 454/324; 454/337
[58] Field of Search ................... 454/229, 75, 324, 454/337, 233; 62/78, 262

[56] References Cited

U.S. PATENT DOCUMENTS

| | | | |
|---|---|---|---|
| 4,838,344 | 6/1989 | Murakami | 165/48.1 |
| 4,919,197 | 4/1990 | Murakami | 165/48.1 |
| 5,297,988 | 3/1994 | Nishino et al. | 454/75 |
| 5,302,359 | 4/1994 | Nowatzki | 422/306 |

*Primary Examiner*—Harold Joyce
*Assistant Examiner*—Derek S. Boles
*Attorney, Agent, or Firm*—Burns, Doane, Swecker & Mathis, L.L.P.

[57] ABSTRACT

An indoor air conditioner includes a body having an air inlet, an air outlet, a heat exchanger disposed in an air flow path between the air inlet and outlet, and a blower for drawing room air into the body through the air inlet, and discharging the air back into the room after the air has exchanged heat with the heat exchanger. A controller provides signals for starting up and shutting down the air conditioner. A deodorizer, such as an ozonizer or negative ion generator, is disposed in the body and is connected to the controller so as to be energized for a predetermined period during start-up, and to be energized for a predetermined period after shutdown. During start-up, the energizing of the deodorizer begins before the blower is actuated. After shutdown, the deodorizer continues to be energized after the blower is deactivated. The deodorizer is thus able to deodorize the inside of the body while the blower is inactive, to prevent unpleasant air from being emitted when the blower is actuated.

12 Claims, 5 Drawing Sheets

METHOD AND APPARATUS FOR DEODORIZING THE INTERIOR OF A ROOM AIR CONDITIONER

BACKGROUND OF THE INVENTION

1. Field of the Invention

The present invention relates to a deodorizing apparatus of an air conditioner for removing odor generated by humidity in an air indoor unit and a control method thereof.

2. Description of the Prior Art

Generally, a conventional air conditioner is disclosed in Japanese laid open patent application No. Heisei 2-309148.

As illustrated in FIG. 1, the air conditioner disclosed in the Japanese application is constituted by an indoor unit provided with a variable speed blower 112, a suction and discharge duct for supplying into respective rooms the air discharged out of the indoor unit, a wind control damper disposed at respective terminal units of the duct, a ventilation duct for returning the air into respective rooms and an external air infuse duct arranged at a ventilation side. The air conditioner further includes damper opening and closing detecting means 100 for detecting an opening and closing state of the wind control damper for each room, a wind intensity detecting means 102 for detecting wind intensity, a detecting means 104 for detecting both an opening and closing state of the wind control damper (according to a signal from the damper opening and closing detecting means 100) and the wind intensity (according to a signal from the wind intensity detecting means 102), a wind intensity determining means 106 for determining a required or necessary wind intensity based on the detection of the opening and closing of the wind control damper and the detection of the wind intensity, a blower revolution determination control means 108 for determining a required blower speed for achieving the required wind intensity, and a blower revolution control means 110 for controlling the speed of the blower 112.

In the thus-constructed air conditioner, the opening and closing state of the wind control damper for each room is detected and used to determine a required blown wind intensity, and a comparison is made between such required wind intensity and the detected blown wind intensity to thereby change the speed of the blower, so that the wind intensity can be stably supplied to each room. However there is a problem in that an unpleasant odor such as fungus odor and the like cannot be eliminated that is generated by a large quantity of humidity occurring at a periphery of an evaporator due to a temperature difference between an inner temperature of the indoor unit and the room air.

SUMMARY OF THE INVENTION

The present invention is therefore disclosed to solve the afore-mentioned problem and it is an object of the present invention to provide a deodorizing apparatus of an air conditioner and a control method thereof for removing unpleasant odor generated by humidity in an indoor unit.

In accordance with one aspect of the present invention, there is provided a deodorizing apparatus of an air conditioner constituted by a suction inlet for sucking room air, an indoor heat exchanger for heat-exchanging the room air sucked through the suction inlet, a discharge outlet for discharging the air heat-exchanged by the indoor heat exchanger and a discharge outlet door for opening and closing the discharge outlet so as to prevent foreign objects or dust from being infused into an indoor unit through the discharge outlet, the deodorizing apparatus comprising:

control means; and deodorizer driving means for controllably driving a deodorizer so as to remove odor from the indoor unit according to control of the control means when a operation start signal and an operation stop signal are received.

In accordance with another aspect of the present invention, there is provided a control method of a deodorizing apparatus of an air conditioner, the method comprising the steps of:

driving the deodorizer for a predetermined period of time so as to remove odor from the indoor unit when the operation start signal and the operation stop signal are input during a normal operation; and opening and closing a discharge outlet of driving a discharge outlet door after the deodorizer is driven at the deodorizer driving step.

BRIEF DESCRIPTION OF THE DRAWINGS

For a thorough understanding of the nature and objects of the invention, reference should be made to the following detailed description taken in conjunction with the accompanying drawings in which.

DETAILED DESCRIPTION OF A PREFERRED EMBODIMENT OF THE INVENTION

The embodiment of the present invention will now be described in detail with reference to the accompanying drawings.

Figure 1:
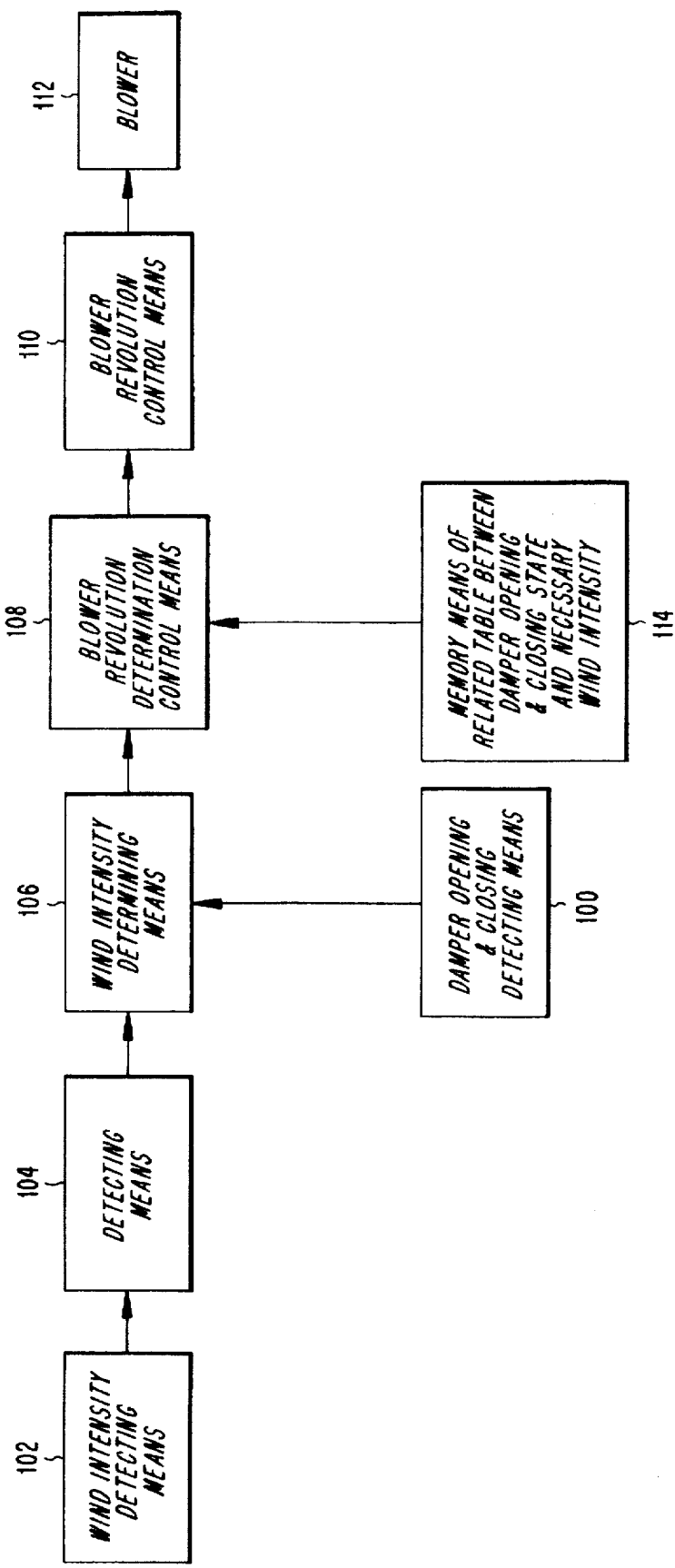
FIG. 1 is a control block diagram of an air conditioner system according to the prior art.
Figure 2:
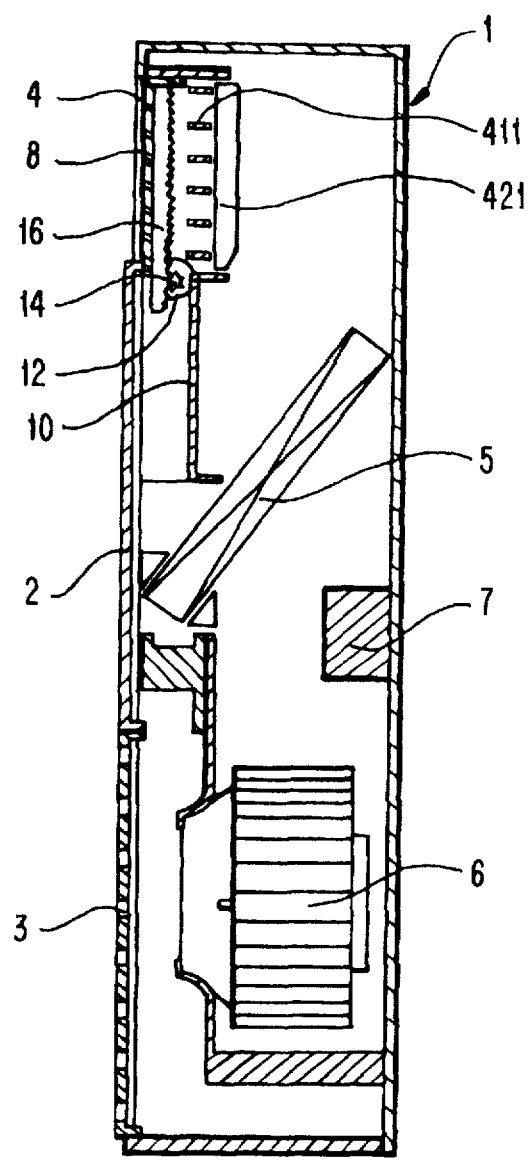
FIG. 2 is a schematic diagram for illustrating an indoor unit of an air conditioner according to an embodiment of the present invention.

As illustrated in FIG. 2, reference numeral 1 defines an indoor unit body (hereinafter referred to as indoor unit) of an air conditioner, where the front of the indoor unit 1 is coupled to a cover member 2.

The indoor unit 1 is formed at a front lower area thereof with a suction inlet 3 for conducting an inflow of room air and is formed at an upper front area thereof with a discharge outlet 4 for discharging the heat-exchanged air (cool wind or warm wind) into the room.

The discharge outlet 4 is provided with an up and down wind direction control vane 411 and a left and right wind direction control vane 421 for controlling directions of the air discharged into the room.

Furthermore, the indoor unit 1 is arranged at an approximate inner center thereof with an indoor heat exchanger 5 so as to heat-exchange (heat or cool) the room air sucked through the suction inlet 3 by way of latent heat of a refrigerant. The indoor heat exchanger 5 is provided with an indoor fan 6 for sucking the room air through the suction inlet 3 and simultaneously for discharging heat-exchanged air through the discharge outlet 4.

The indoor fan 6 is disposed adjacent to a deodorizer 7 for removing odor generated by humidity in the indoor unit 1.

The discharge outlet 4 is formed therein with a discharge outlet door 8 able to be vertically driven for opening the discharge outlet 4 so as to smoothly supply heat-exchanged air during operation of the air conditioner and to prevent the dust, foreign objects and the like from being infused into the indoor unit 1 through the discharge outlet 4 during a stand-by operation of the air conditioner and to close the discharge outlet 4 for a neater appearance thereof.

Meanwhile, driving means for vertically driving the discharge outlet door 8 includes a supporting member 10 fixedly coupled to an upper portion of the indoor unit 1, a door motor 12 fixedly coupled to the supporting member 10 to generate an electric power for vertically moving the discharge outlet door 8, a pinion gear 14 coupled to an axis of the door motor 12 so as to be rotated by the door motor 12, and a rack gear 16 for transforming the rotary motion of the pinion gear 16 to rectilinear motion so that the discharge outlet door 8 can be vertically transported in cooperation with the pinion gear 14 during rotation thereof.

Next, the control block diagram for removing odor generated from the indoor unit thus constructed will be described in detail with reference to FIG. 3.

Figure 3:
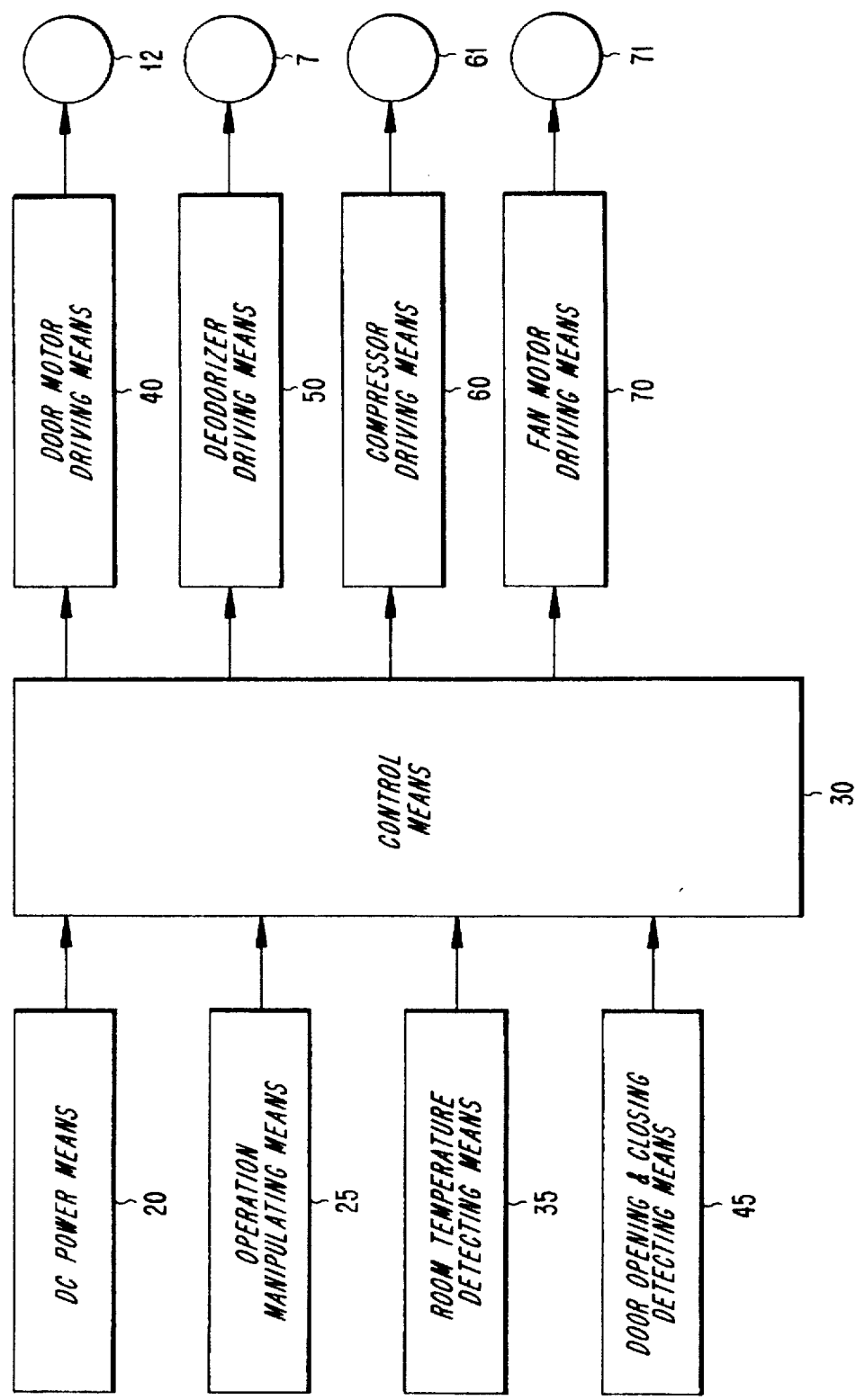
FIG. 3 is a control block diagram of a deodorizer of an air conditioner according to the embodiment of the present invention.

As illustrated in FIG. 3, direct current DC electric power means 20 serves to receive a power source voltage of commercial alternating current electric power supplied from an AC power source input terminal and to transform same into a predetermined DC voltage necessary for operation of the air conditioner.

Operation manipulating means 25 is adapted to be provided with a plurality of functional keys (associated with artificial intelligence, cooling, air cleaning, booked operation, stop and the like) so as to input operation conditions desired by a user, and also is provided with a signal input key so as to input an operation start signal and an operation stop signal for the air conditioner.

Control means 30 is a microcomputer which serves to receive the DC voltage output from the DC power means 20 to initialize the air conditioner, and, at the same time, to control overall operations of the air conditioner according to an operation selecting signal and an operation and stop signal input from the operation manipulating means 25. The control means 30 is inherently provided with a timer for counting a driving time of a deodorizer 7.

Room temperature detecting means 35 is adapted to control a room temperature to a reference temperature (Ts) established by the user using the operation manipulating means 25, to thereby detect an actual temperature (Tr) of the room air sucked through the suction inlet 3 so as to perform cooling and heating operations of the air conditioner.

Door motor driving means 40 serves to receive a control signal output from the control means 25 when the operational start signal and the operation stop signal are received from the operation manipulating means 25 to controllably drive the door motor so that the discharge outlet door 8 for opening and closing the discharge outlet 4 can be vertically moved.

Furthermore, door opening and closing detecting means 45 serves to detect whether the discharge outlet door 4 is opened or closed and to output the detected result to the control means 30.

Deodorizer driving means 50 is adapted to receive a control signal from the control means 30 and to drive the deodorizer 7 for removal of odor caused by humidity in the indoor unit 1 when the operation start signal is received. The deodorizer driving means 50 is an electrical device such as an ozonizer or a negative ion apparatus or the like.

Compressor driving means 60 serves to receive a control signal from the control means 30 according to a difference between the reference temperature (Ts) established by the user according to the operation manipulating means 25 and the actual room temperature (Tr) detected by the room temperature detecting means 35, to controllably drive a compressor 61.

Fan motor driving means 70 is adapted to receive a control signal from the control means 30 to energize an indoor fan motor 71 which drives the indoor fan 6.

Figure 4A:
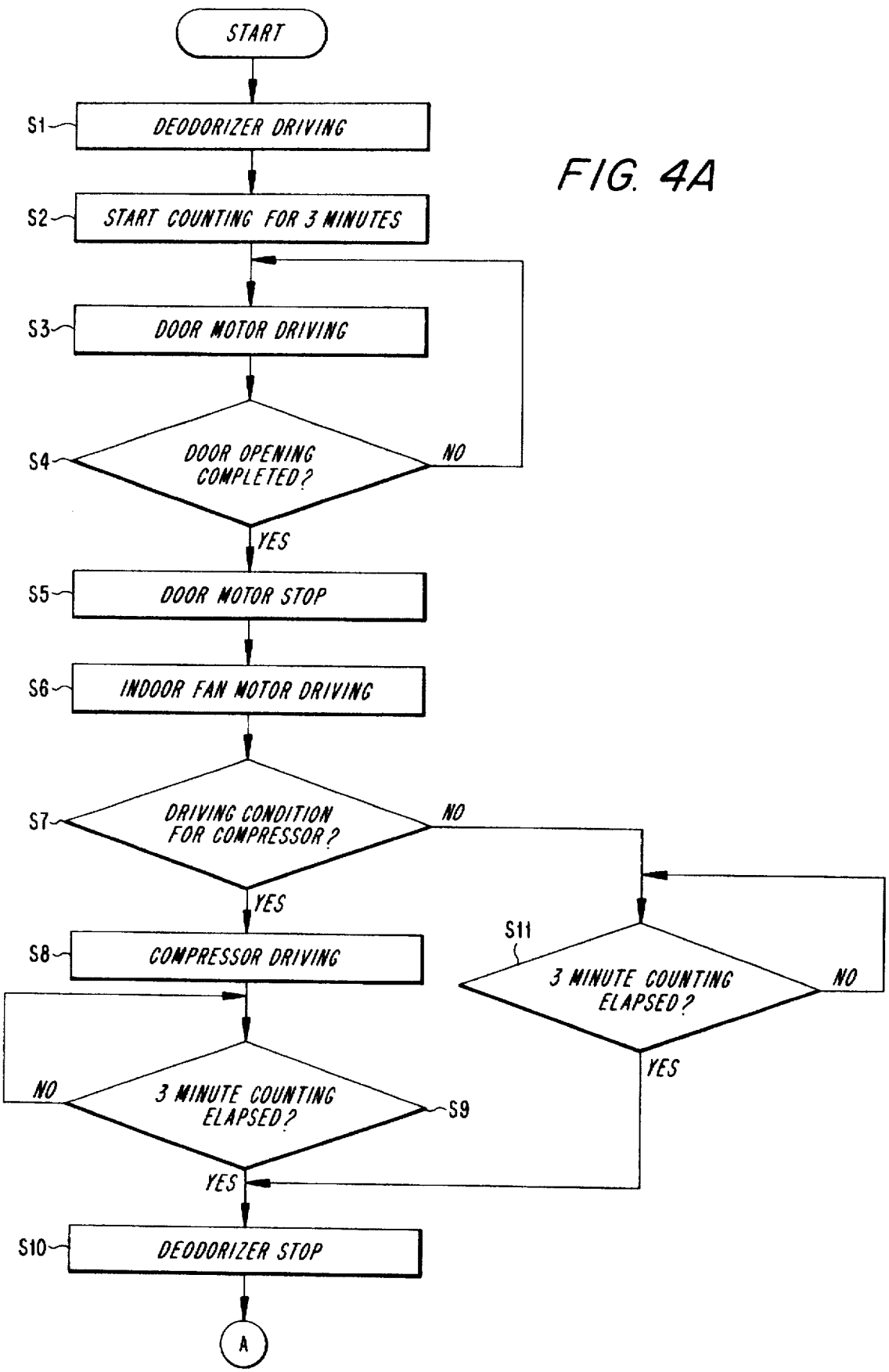
FIGS. 4A and 4B are flow charts for illustrating deodorizing procedures of an air conditioner according to the present invention.
Figure 4B:
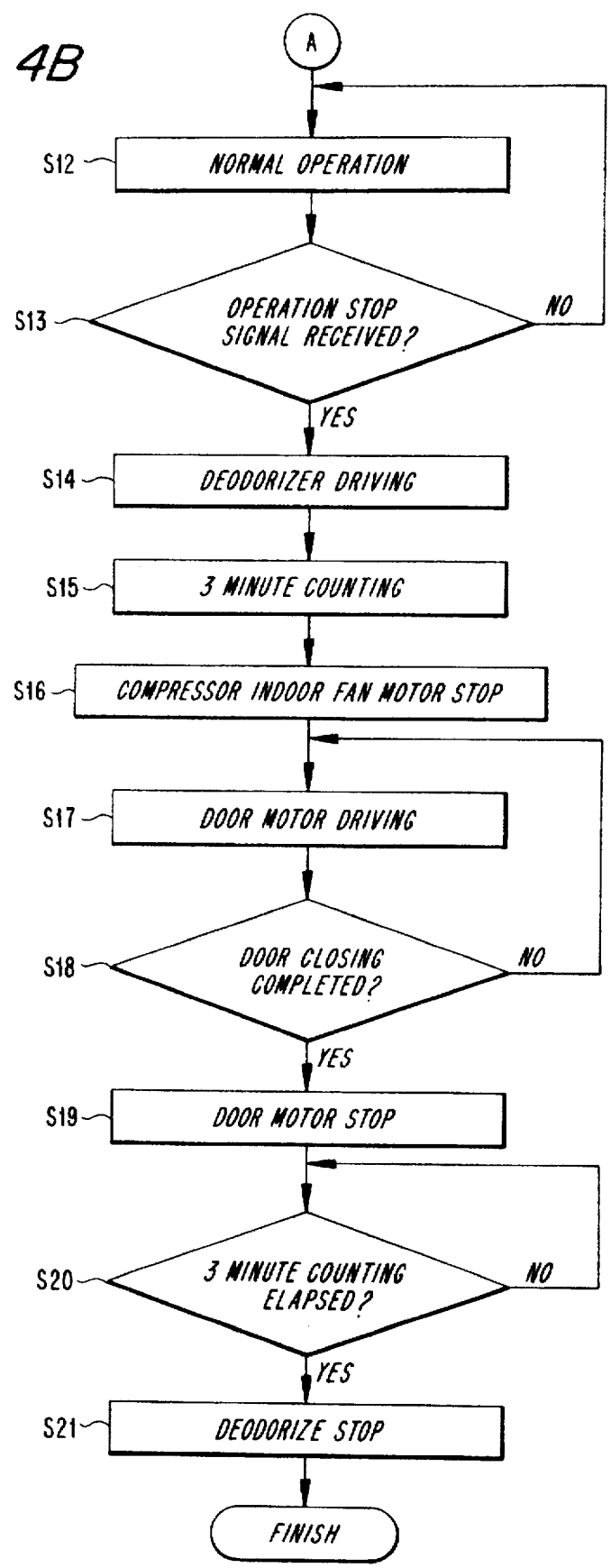

Now, the operation of the deodorizing apparatus of an air conditioner thus constructed will be described with reference to FIGS. 4A and 4B.

As an initial condition for describing the operation of the present invention, it is assumed that the discharge outlet 4 is closed.

First of all, the DC power means 20 serves to convert the commercial AC power to a predetermined DC voltage necessary for driving the air conditioner, and to output same to respective driving circuits and the control means 30.

The control means 30 serves to receive the DC voltage output from the DC power means 20 to initialize the air conditioner.

At this time, when the user manipulates the operation manipulating means 25 to select a desired manipulating command and inputs an operation manipulating signal, the control means at step S1 serves to output to the deodorizer driving means 50 a control signal for driving the deodorizer 7.

Subsequently, the deodorizer driving means 50 serves to drive the deodorizer 7 according to the control of the control means 30, to thereby remove odor from the indoor unit, and at step S2, a driving time of the deodorizer 7 is counted by a timer inherently disposed in the control means 30.

During this time period, at step S3, the control means 30 outputs to the door motor driving means 40 a control signal for opening the closed discharge outlet 4.

Then, the door motor driving means 40 serves to drive the door motor 12 according to the control of the control means, so that the pinion gear 14 is rotated downward along the rack gear 16, thereby lowering the discharge output door 8 and opening the discharge outlet 4.

Successively, at step S4, a lowered position of the discharge outlet door 8 is detected by the door opening and closing detecting means 45, and the control means 30 serves to receive a signal from the door opening and closing detecting means 45 to determine whether the discharge outlet 4 is completely opened.

As a result of the discrimination at step S4, if the discharge outlet 4 is not completely opened (in case of no), flow returns to step S3, and continuously drives the door motor 12 until the discharge outlet 4 is completely opened.

If the discharge outlet 4 is completely opened (in case of yes), flow proceeds to step S5, where the door motor driving means 40 serves to stop the activation of the door motor 12 according to the control of the control means 30.

Meanwhile, it takes approximately 10 seconds to completely open the discharge outlet 4.

When the discharge outlet 4 is completely opened, the control means 30 serves at step S6 to provide the fan motor driving means 70 with a control signal.

Subsequently, the fan motor driving means 70 controls the speed of the indoor fan motor 71 according to the control of the control means 30 to thereby drive the indoor fan 6.

When the indoor fan 6 is driven, the room air is sucked into the indoor unit through the suction inlet 3, and is directed past the deodorizer 7 and through the heat exchanger 5 before being discharged back into the room. Also, at this time, the actual temperature (Tr) of the room air sucked through the suction inlet 3 is detected by the room temperature detecting means 35.

Successively, at step S7, a comparison is made between the room actual temperature (Tr) and the reference temperature (Ts) established by the user, thereby discriminating whether the compressor 61 needs to be actuated.

That is, assuming at step S7 that either: (A) for a cooling operation it is determined that the actual room temperature (Tr) is greater than the reference temperature (Ts), or (B) for a heating operation it is determined that the actual room temperature (Tr) is less than the reference temperature (Ts); in either case the answer is yes.

As a result, flow advances to step S8, where the control means 30 serves to determine an operational frequency of the compressor 61 according to the difference between the room temperature (Tr) and the reference temperature (Ts) to thereby cause a control signal for driving the compressor 61 to be supplied to the compressor driving means 60.

Subsequently, the compressor driving means 60 is adapted to drive the compressor 61 according to the operational frequency determined by the control means 30.

At step S9, a discrimination is made as to whether the driving time of the deodorizer 7, counted by the control means 30 beginning at the moment the deodorizer 7 is first driven, has reached 3 minutes, and if the driving time has not reached 3 minutes (in case of no), flow returns to step S9, and keeps counting until the driving time reaches 3 minutes.

As a result of discrimination at step S9, if the driving time has reached 3 minutes (in case of yes), flow advances to step S10, and serves to stop activation of the deodorizer 7, so that odor removal from the indoor unit 1 is completed.

Meanwhile, if the result of the discrimination at step S7 is not to drive the compressor 61 (in case of no), flow advances to step S1, and discriminates whether the driving time of the deodorizer 7 has reached 3 minutes.

If 3 minutes have not elapsed (in case of no), flow returns to step S11, and keeps counting until 3 minutes elapse.

As a result of the discrimination at step S11, if the driving time has reached 3 minutes (in case of yes), flow proceeds to step S10, and performs repeated operations subsequent to step S10.

In other words, when the operation start signal of the air conditioner is received, the deodorizer 7 is driven firstly before activation of the indoor fan motor 71, thereby removing odor from the indoor unit 1.

The driving of the indoor fan motor 71 is delayed for approximately 10 seconds to enable the opening of the discharge outlet 4, but because the deodorizer 7 is driven during that period, the odor in the interior of the indoor unit 1 can be completely eliminated for ensuring a discharge of pleasant air into the room.

When the deodorizer 7 is stopped at step S12, the air heat-exchanged continues to be discharged for performing the indoor air conditioning.

At this time, at step S13, a discrimination is made as to whether the operation stop signal has been received from the operation manipulating means 25 during the normal operation of the air conditioner, and if the operation stop signal has not been received (in case of no), flow returns to step S12 and continuously executes normal operational performances.

As a result of the discrimination at step S13, if the operation stop signal has been received during the normal operation (in case of yes), flow proceeds to step S14, where the control means 30 serves to re-activate the deodorizer 7 to remove the odor from the indoor unit during input of the operation stop signal.

Successively, at step S15, the timer inherently disposed in the control means serves to start counting the time so that the deodorizer 7 can be driven for only 3 minutes. During this time, at step S16, the control means 30 serves to generate a control signal for stopping the compressor 61 and the indoor fan 6.

Successively, at step S17, the control means 30 serves to generate to the door motor driving means 40 a control signal for closing the opened discharge outlet 4.

Consequently, the door motor driving means 40 serves to drive the door motor 12 according to the control of the control means 30 to vertically rotate the pinion gear 14 meshed thereto along the rack gear 16, so that the discharge outlet door 8 is vertically operated to close the discharge outlet 4.

Successively, at step S18, position of the discharge outlet door 8 upwardly moved by the activation of the door motor 12 is detected by the door opening and closing detecting means 45, and the control means 30 receives a signal from the door opening and closing detecting means 45 to thereby discriminate whether the discharge outlet 4 has been completely closed.

As a result of the discrimination at step S18, if the discharge outlet 4 has not been completely closed (in case of no), flow returns to step S17 and keeps driving the door motor 12 until the discharge outlet 4 is completely closed.

If the discharge outlet 4 is completely closed (in case of yes), flow advances to step S19, where the door motor driving means 40 stops the activation of the door motor 12 according to the control of the control means 30.

Successively, at step S20, a discrimination is made as to whether the activation time of the deodorizer has reached 3 minutes. If 3 minutes has not elapsed (in case of no), flow returns to step S20, and keeps counting the activation time of the deodorizer until the 3-minute time passes.

As a result of the discrimination at step S20, if the activation time has reached the 3-minute period (in case of yes), flow proceeds to step S21, where the deodorizer 7 is stopped and the operation is finished.

As mentioned above, when the operation stop signal is received during the normal operation, the deodorizer 7 is instantly activated for 3 minutes to thereby remove the odor from the indoor unit 1 and the air conditioner finishes the operation.

As is apparent from the foregoing, there is an advantage in that, when an operation start signal is received, a deodorizer is instantly activated for 3 minutes to remove the odor from an indoor unit before and after the activation of the fan, and even when an operation stop signal is received during a normal operation, the deodorizer is instantly activated for 3 minutes to thereafter finish the operation, so that the odor inside the indoor unit can be completely eliminated and pleasant air can be dispatched into and circulated in a room during a re-operation of the air conditioner.

Having described a specific preferred embodiment of the invention with reference to the accompanying drawings, it is to be understood that the invention is not limited to that precise embodiment, and that various changes and modifications may be effected therein by one skilled in the art without departing from the scope or spirit of the invention as defined in the appended claims.

What is claimed is:

1. An indoor air conditioner comprising:

a body forming an air inlet and an air outlet;

a heat exchanger disposed in an air flow path between the air inlet and outlet;

an electrically energized deodorizer disposed in the body for deodorizing air therein; and a control mechanism for controlling start-up and shutdown of the air conditioner, the control mechanism connected to the deodorizer for energizing the deodorizer for a predetermined period during start-up of the air conditioner and for a predetermined period after shutdown of the air conditioner, to deodorize the interior of the body.

2. The indoor air conditioner according to claim 1 wherein the deodorizer is an ozone generator.

3. The indoor air conditioner according to claim 1 wherein the deodorizer is a negative ion generator.

4. The indoor air conditioner according to claim 1 further including a door for opening and closing the air outlet, and a door moving mechanism for moving the door between open and closed positions; the control mechanism being connected to the door moving mechanism for opening the door during a part of the period in which the deodorizer is energized during start-up of the air conditioner.

5. The indoor air conditioner according to claim 1, further including a blower for circulating air from the air inlet to the air outlet; the control mechanism being connected to the blower for actuating the blower after the energizing of the deodorizer has begun, during start-up of the air conditioner.

6. The indoor air conditioner according to claim 1, further including a blower for circulating air from the air inlet to the air outlet; the control mechanism being connected to the blower for deactivating the blower before deenergizing the deodorizer.

7. The indoor heat exchanger according to claim 1 wherein the control mechanism includes a timer for counting the predetermined period.

8. In a method of operating a room air conditioner wherein air from a room is directed across a heat exchanger within a body before being discharged back into the room, and wherein a controller supplies start-up and shutdown signals to the air conditioner, the improvement comprising the steps of energizing an electrically energizable deodorizer disposed within the body for a predetermined period during air conditioner start-up, and for a predetermined period after air conditioner shutdown, to deodorize the interior of the body.

9. The method according to claim 8 wherein a door is provided for opening and closing an air outlet of the body; a door moving mechanism is connected to the door; the controller is connected to the door moving mechanism; and further comprising the step of opening the door during a part of the period in which the deodorizer is energized during start-up of the air conditioner.

10. The method according to claim 8 wherein a blower is provided for circulating air from an air inlet to an air outlet of the body; the controller being connected to the blower; and further comprising the step of actuating the blower after the deodorizer has been energized, during start-up of the air conditioner.

11. The method according to claim 8 wherein a blower is provided for circulating air from an air inlet to an air outlet of the body; the controller being connected to the blower; and further comprising the step of energizing the deodorizer so that, upon shutdown of the air conditioner, the deodorizer remains energized after the blower has been deactuated.

12. The method according to claim 8 wherein the predetermined period is about three minutes.

* * * * *